United States Patent
Kiyose

(10) Patent No.: US 10,424,720 B2
(45) Date of Patent: Sep. 24, 2019

(54) PIEZOELECTRIC DEVICE, PIEZOELECTRIC MODULE, AND ELECTRONIC APPARATUS

(71) Applicant: Seiko Epson Corporation, Tokyo (JP)

(72) Inventor: Kanechika Kiyose, Matsumoto (JP)

(73) Assignee: Seiko Epson Corporation (JP)

( * ) Notice: Subject to any disclaimer, the term of this patent is extended or adjusted under 35 U.S.C. 154(b) by 462 days.

(21) Appl. No.: 15/350,491

(22) Filed: Nov. 14, 2016

(65) Prior Publication Data
US 2017/0155029 A1   Jun. 1, 2017

(30) Foreign Application Priority Data

Nov. 30, 2015   (JP) .................................. 2015-234291

(51) Int. Cl.
| | | |
|---|---|---|
| A61B 8/00 | (2006.01) | |
| B06B 1/06 | (2006.01) | |
| H01L 41/04 | (2006.01) | |
| H01L 41/08 | (2006.01) | |
| H01L 41/047 | (2006.01) | |

(52) U.S. Cl.
CPC ............ *H01L 41/0825* (2013.01); *A61B 8/44* (2013.01); *A61B 8/4483* (2013.01); *A61B 8/4494* (2013.01); *B06B 1/0622* (2013.01); *H01L 41/042* (2013.01); *H01L 41/0475* (2013.01)

(58) Field of Classification Search
CPC .............. H01L 41/0825; H01L 41/042; H01L 41/0474; H01L 41/0475; B61B 1/0622; A61B 8/44; A61B 8/4183; A61B 8/4494

USPC ......................................... 310/322, 334, 365
See application file for complete search history.

(56) References Cited

U.S. PATENT DOCUMENTS

| | | | | |
|---|---|---|---|---|
| 6,211,853 B1* | 4/2001 | Takeuchi | ............... | G02B 26/08 |
| | | | | 345/108 |
| 2002/0080129 A1* | 6/2002 | Takeuchi | ................ | G09F 9/305 |
| | | | | 345/204 |

(Continued)

FOREIGN PATENT DOCUMENTS

| | | |
|---|---|---|
| JP | 2003-235098 A | 8/2003 |
| JP | 2008-118631 A | 5/2008 |

(Continued)

*Primary Examiner* — Thomas M Dougherty
(74) *Attorney, Agent, or Firm* — Harness, Dickey & Pierce, P.L.C.

(57) ABSTRACT

A piezoelectric device includes an element substrate that includes a first surface (operating surface) and a second surface (back surface) on a side opposite to the first surface, and includes a recessed opening provided on the first surface and a supporting portion surrounding the recessed opening, a piezoelectric body that is provided on the second surface of the recessed opening, a plurality of connection electrodes (lower connection electrode and upper connection electrode) that are connected to the piezoelectric body and are drawn to the second surface of the supporting portion from the piezoelectric body, a reinforcement plate that is bonded to the second surface side of the element substrate, and a plurality of through electrodes that are provided at a position of the reinforcement plate which faces the supporting portion, pass through the reinforcement plate in a thickness direction, and are respectively connected to the plurality of connection electrodes.

7 Claims, 9 Drawing Sheets

(56) References Cited

U.S. PATENT DOCUMENTS

| | | | |
|---|---|---|---|
| 2003/0025442 A1* | 2/2003 | Takeuchi | G02B 26/004 |
| | | | 313/495 |
| 2003/0043449 A1* | 3/2003 | Takeuchi | G02B 26/02 |
| | | | 359/290 |
| 2005/0140248 A1 | 6/2005 | Kuniyasu et al. | |
| 2008/0089181 A1 | 4/2008 | Adachi et al. | |
| 2009/0034370 A1* | 2/2009 | Guo | B06B 1/0622 |
| | | | 367/180 |
| 2011/0071396 A1 | 3/2011 | Sano et al. | |
| 2011/0291525 A1* | 12/2011 | Maruyama | H02N 2/0015 |
| | | | 310/334 |
| 2012/0188849 A1 | 7/2012 | Matsuda et al. | |

FOREIGN PATENT DOCUMENTS

| | | |
|---|---|---|
| JP | 2011-255024 A | 12/2011 |
| JP | 2012-152319 A | 8/2012 |
| WO | WO-2009-139400 A1 | 11/2009 |

* cited by examiner

US 10,424,720 B2

PIEZOELECTRIC DEVICE, PIEZOELECTRIC MODULE, AND ELECTRONIC APPARATUS

BACKGROUND

1. Technical Field

The present invention relates to a piezoelectric device, a piezoelectric module, and an electronic apparatus.

2. Related Art

In the related art, an ultrasonic sensor including a plurality of ultrasonic transducers mounted on a sensor substrate has been known (for example, JP-A-2012-152319).

The ultrasonic sensor disclosed in JP-A-2012-152319 mentioned above includes, for example, a matrix-like two-dimensional array structure in which four ultrasonic transducers are disposed on the sensor substrate at equal intervals along an X-axis and a Y-axis. However, such a two-dimensional array structure has a problem that wirings connected to the ultrasonic transducers become complicated.

In order to solve the above-described problem, an ultrasonic probe using a through electrode has been known (for example, Pamphlet of International Publication WO 2009/139400).

The ultrasonic probe disclosed in Pamphlet of International Publication WO 2009/139400 mentioned above includes a plurality of vibration elements each of which an electromechanical coupling coefficient or sensitivity changes depending on a bias voltage. Each of the vibration elements includes a substrate, a first film provided on the substrate, a lower electrode provided within the first film, a frame provided on the first film, a second film provided on the frame, and an upper electrode provided within the second film. In addition, the frame is provided with an opening, and an internal space (vacuum) is formed between the first film and the second film by the opening. This cMUT chip applies a pulse voltage between the lower electrode and the upper electrode to thereby vibrate the second film facing the internal space and transmit ultrasonic waves to a side opposite to the substrate.

Through holes passing through the substrate, that is, through electrodes are provided corresponding to the upper electrode and the lower electrode of the cMUT chip, and the through electrodes are connected to a signal pattern provided on a flexible substrate through the substrate. With such a configuration, the simplification of wirings is achieved.

Incidentally, in the ultrasonic probe disclosed in Pamphlet of International Publication WO 2009/139400 mentioned above, the simplification of wirings is achieved by the through electrodes, and the through electrodes are provided in the substrate. Accordingly, the strength of the element substrate is reduced, which leads to a tendency for the element substrate to be damaged. On the other hand, a configuration in which the element substrate is strengthened by providing a reinforcement plate (sealing plate) is also considered. However, the above-mentioned cMUT chip is configured such that ultrasonic waves are output by vibrating the second film side, and thus a reinforcement plate cannot be provided on the second film side. Accordingly, in a case where a reinforcement plate is provided, it is necessary to provide the reinforcement plate on a side opposite to the first and second films of the substrate. In this case, finally, through electrodes are provided in both the reinforcement plate and the substrate, which results in a problem of the insufficiency of strength.

SUMMARY

An advantage of some aspects of the invention is to provide a piezoelectric device having appropriate strength, a piezoelectric module, and an electronic apparatus.

A piezoelectric device according to an application example of the invention includes an element substrate that includes a first surface and a second surface on a side opposite to the first surface, and includes a recessed opening provided on the first surface and a supporting portion surrounding the recessed opening, a piezoelectric body that is provided on the second surface of the recessed opening, a plurality of connection electrodes that are connected to the piezoelectric body and are drawn to the second surface of the supporting portion from the piezoelectric body, a reinforcement plate that is bonded to the second surface side of the element substrate, and a plurality of through electrodes that are provided at a position of the reinforcement plate which faces the supporting portion, pass through the reinforcement plate in a thickness direction, and are respectively connected to the plurality of connection electrodes.

In this application example, the recessed opening and the supporting portion are provided on the first surface of the element substrate, and the piezoelectric body is provided on the second surface of the recessed opening. The plurality of through electrodes passing through the reinforcement plate in the thickness direction, bonded to the second surface side of the element substrate, are respectively connected to the plurality of connection electrodes connected to the piezoelectric body.

In such a configuration, it is possible to individually control the plurality of connection electrodes by the plurality of through electrodes. In addition, since the through electrodes are configured to be provided in the reinforcement plate rather than being provided in the element substrate, the strength of the element substrate is higher than that in, for example, a configuration in which a through hole or a through electrode is provided in an element substrate, and thus it is possible to suppress damage due to an impact or the like. In addition, although a configuration in which the through electrode is provided in the reinforcement plate is adopted, the reinforcement plate has strength which is sufficiently higher than that of the element substrate, and thus it is possible to suppress the damage of the piezoelectric device. Furthermore, a configuration in which the through electrode is used is adopted, and thus it is also possible to suppress a defect such as a short-circuit, as compared to a configuration in which the connection electrode is connected to a wiring substrate through, for example, wire bonding.

In addition, the connection electrodes provided in the element substrate are electrically connected to the through electrodes, and the through electrodes pass through to a side of the reinforcement plate which is opposite to the element substrate. In this case, one end of each of the through electrodes on a side opposite to the element substrate can be directly bonded to a desired position of the wiring substrate (so-called face-down mounting). Accordingly, for example, in a case where the piezoelectric device is used as an ultrasonic device, it is possible to simplify an operation process at a stage of mounting the piezoelectric device and to improve manufacturing efficiency.

In addition, for example, the connection electrodes are not required to be pulled around to an outer peripheral end of the element substrate, and thus it is possible to achieve the simplification of a wiring configuration. In addition, a terminal region for performing connection of the connection electrodes and a wiring substrate is not required to be provided at the outer peripheral end of the element substrate, and thus it is possible to achieve a reduction in the size of the element substrate.

A piezoelectric module according to an application example of the invention includes an element substrate that includes a first surface and a second surface on a side opposite to the first surface, and includes a recessed opening provided on the first surface and a supporting portion surrounding the recessed opening, a piezoelectric body that is provided on the second surface of the recessed opening, a plurality of connection electrodes that are connected to the piezoelectric body and are drawn to the second surface of the supporting portion from the piezoelectric body, a reinforcement plate that is bonded to the second surface side of the element substrate, a plurality of through electrodes that are provided at a position of the reinforcement plate which faces the supporting portion, pass through the reinforcement plate in a thickness direction, and are respectively connected to the plurality of connection electrodes, a piezoelectric element substrate that is configured such that element units each of which is constituted by the recessed opening and the piezoelectric body are arranged in an array therein, and an input and output circuit that independently inputs and outputs a signal from and to each of the through electrodes.

In the piezoelectric module of this application example, it is possible to suppress a deterioration in the strength of the element substrate and to improve the strength of the piezoelectric element substrate, similar to the above-mentioned piezoelectric device.

In addition, there is a configuration in which a signal is independently input and output with respect to each of the through electrodes from the input and output circuit, and thus it is possible to individually control the elements and to drive the element units with a high level of accuracy.

In other words, in a configuration as disclosed in JP-A-2012-152319 described above, a common electrode (COM) is common to (connected to each other) the plurality of elements, and an SIG (driving electrode) is also common thereto. Accordingly, the plurality of elements are driven as one element group. However, in such a configuration, in the plurality of elements to which the COM and the SIG are common, a voltage drop of a signal occurs in an element distant from an input position of the signal, which results in deterioration in driving accuracy.

On the other hand, in this embodiment, the through electrodes are provided with respect to the respective element units, and thus it is possible to independently drive the element units. Accordingly, the above-mentioned voltage drop of a signal does not occur, and thus it is possible to drive the element units with a high level of accuracy. In addition, the element units are independent of each other, and are thus allowed to function as a two-dimensional array structure. In other words, the transmission of ultrasonic waves can be controlled for each element unit, and thus it is possible to control a transmission direction of ultrasonic waves without using, for example, an acoustic lens and the like.

In the piezoelectric module of the application example, it is preferable that the element units are arranged in an array along a first direction and a second direction intersecting the first direction in a plan view when seen from normal directions of the first surface and the second surface, and each of the connection electrodes includes a first connection electrode which is drawn from the piezoelectric body along the first direction, and a second connection electrode which is drawn from the piezoelectric body along the second direction.

In the piezoelectric module of the application example with this configuration, since the first connection electrode is drawn along the first direction and the second connection electrode is drawn along the second direction intersecting the first direction, and thus it is possible to densely dispose the element units in the piezoelectric module, as compared to a case where both the first connection electrode and the second connection electrode are drawn along the same direction (for example, only in the first direction or only in the second direction). For this reason, it is possible to reduce an array interval and to promote reductions in the sizes of the piezoelectric element substrate and the piezoelectric module.

In the piezoelectric module of the application example, it is preferable that the element units are arranged in an array along a first direction and a second direction intersecting the first direction in a plan view when seen from normal directions of the first surface and the second surface, each of the connection electrodes includes a third connection electrode which is drawn to one end side of the piezoelectric body in the first direction, and a fourth connection electrode which is drawn to the other end side of the piezoelectric body in the first direction, and the third connection electrode is positioned on one end side in the second direction, and the fourth connection electrode is positioned on the other end side in the second direction.

In the piezoelectric module of the application example with this configuration, the third connection electrode is drawn to one end side of each of the element units in the first direction and one end side in the second direction, and the fourth connection electrode is drawn to the other end side of each of the element units in the first direction and the other end side in the second direction. For example, in a case where x- and y-axes passing through the center of each of the element units are specified, the fourth connection electrode is provided on a third quadrant in a case where the third connection electrode is provided on a first quadrant. Meanwhile, in each of the element units, the fourth connection electrode may be provided on a fourth quadrant in a case where the third connection electrode is provided on a second quadrant.

In such a configuration, a third connection electrode of one element unit and a fourth connection electrode of the other element unit in adjacent element units can be disposed lined up along the second direction. According to this configuration, for example, it is possible to densely dispose the element units in the piezoelectric module, as compared to a case where connection electrodes of adjacent element units are lined up along the first direction or the second direction.

In the piezoelectric module of the application example, it is preferable that the element units are arranged in an array along a first direction and a second direction intersecting the first direction in a plan view when seen from normal directions of the first surface and the second surface, the connection electrode connected to a first element unit, among the plurality of elements units, is drawn from the piezoelectric body along the first direction, and the connection electrode connected to a second element unit, which is adjacent to the first element unit, is drawn from the piezoelectric body along the second direction.

In the piezoelectric module of the application example with this configuration, a drawing direction of a connection electrode of the first element unit is different from a drawing direction of a connection electrode of the second element unit. Accordingly, the connection electrode of the first element unit and the connection electrode of the second element unit are not lined up along the first direction or the second direction, and thus it is possible to densely dispose the element units in the piezoelectric module.

An electronic apparatus according to an application example of the invention includes an element substrate that includes a first surface and a second surface on a side opposite to the first surface, and includes a recessed opening provided on the first surface and a supporting portion surrounding the recessed opening, a piezoelectric body that is provided on the second surface of the recessed opening, a plurality of connection electrodes that are connected to the piezoelectric body and are drawn to the second surface of the supporting portion from the piezoelectric body, a reinforcement plate that is bonded to the second surface side of the element substrate, a plurality of through electrodes that are provided at a position of the reinforcement plate which faces the supporting portion, pass through the reinforcement plate in a thickness direction, and are respectively connected to the plurality of connection electrodes, a piezoelectric element substrate that is configured such that element units each of which is constituted by the recessed opening and the piezoelectric body are arranged in an array therein, an input and output circuit that independently inputs and outputs a signal from and to each of the through electrodes, and a control unit that controls the piezoelectric body.

In the electronic apparatus of the application example, it is possible to suppress a deterioration in the strength of the element substrate and to improve the strength of the piezoelectric element substrate, similar to the above-mentioned piezoelectric device. In addition, similarly to the above-mentioned piezoelectric module, a configuration in which a signal is independently input and output with respect to each of the through electrodes from the input and output circuit is adopted, and thus it is possible to individually control the elements and to drive the element units with a high level of accuracy. In this manner, it is possible to perform various processes (for example, the transmission and reception of ultrasonic waves, the detection of pressure, the application of pressure, and the like) in the electronic apparatus with a high level of accuracy by driving the element units with a high level of accuracy.

In the electronic apparatus of the application example, it is preferable that the control unit performs an ultrasonic wave transmission process of driving the piezoelectric body to transmit ultrasonic waves and an ultrasonic wave reception process of receiving ultrasonic waves by the element units, and measures an object to be measured, on the basis of transmission and reception timings of the ultrasonic waves.

In the application example with this configuration, the control unit controls the element units, to thereby perform ultrasonic wave transmission and reception processes and to perform measurement (measurement of ultrasonic waves) on an object to be measured, on the basis of transmission and reception timings of the ultrasonic waves. In this application example, as described above, the ultrasonic wave transmission process and the ultrasonic wave reception process in each of the element units can be performed with a high level of accuracy, and thus it is possible to achieve measurement accuracy in the measurement of ultrasonic waves.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, an ultrasonic measurement apparatus as an electronic apparatus of a first embodiment according to the invention will be described with reference to the accompanying drawings.

Configuration of Ultrasonic Measurement Apparatus 1

Figure 1:
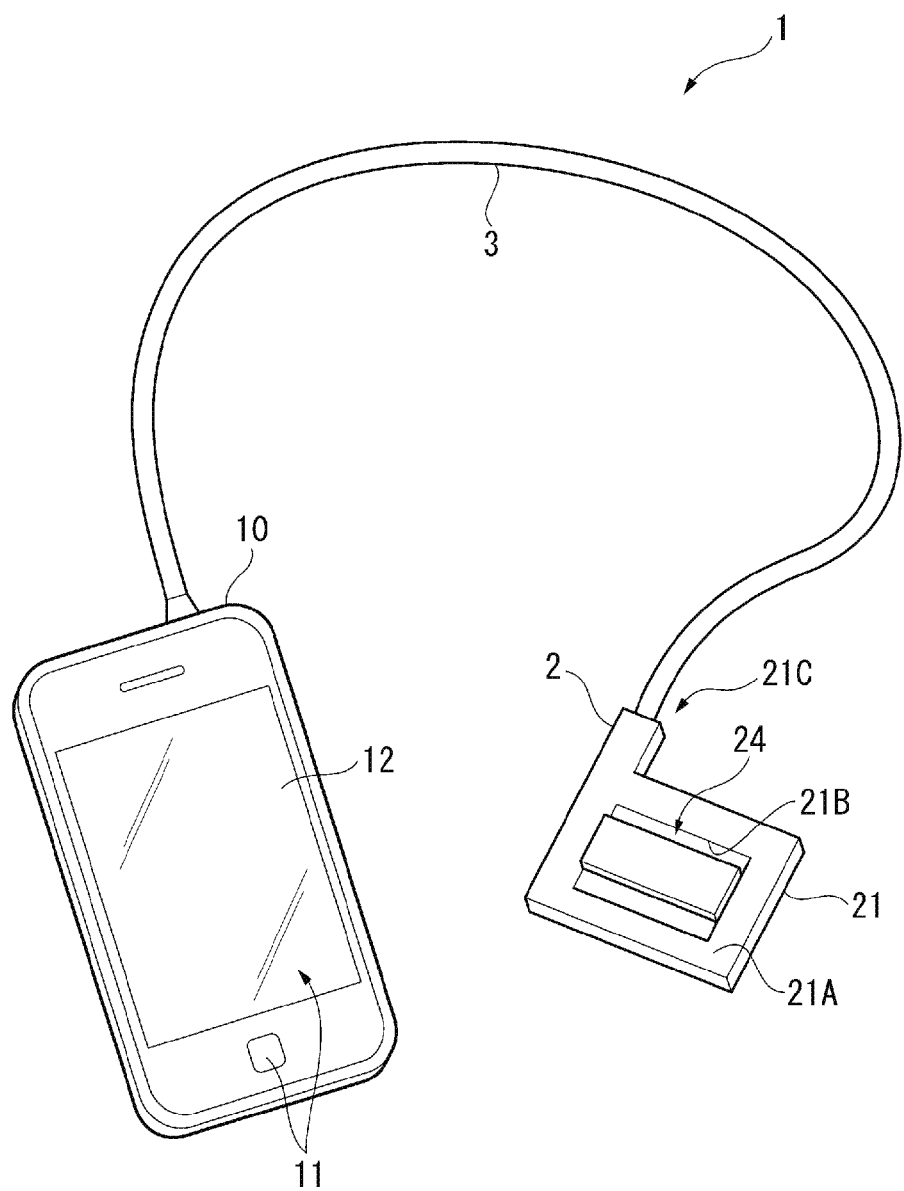
FIG. 1 is a perspective view showing a schematic configuration of an ultrasonic measurement apparatus according to a first embodiment.

FIG. 1 is a perspective view showing a schematic configuration of an ultrasonic measurement apparatus 1 according to this embodiment.

The ultrasonic measurement apparatus 1 of this embodiment includes an ultrasonic probe 2 and a control device 10 which is electrically connected to the ultrasonic probe 2 through a cable 3, as shown in FIG. 1.

The ultrasonic measurement apparatus 1 transmits ultrasonic waves into a living body (for example, a human body) from the ultrasonic probe 2 by making the ultrasonic probe 2 abut on the surface of the living body. In addition, the ultrasonic waves reflected by an organ within the living body are received by the ultrasonic probe 2, thereby acquiring, for example, an internal tomographic image within the living body or measuring conditions (for example, blood pressure, blood flow, and the like) of an organ within the living body, on the basis of a received signal thereof.

Configuration of Control Device 10

Figure 2:
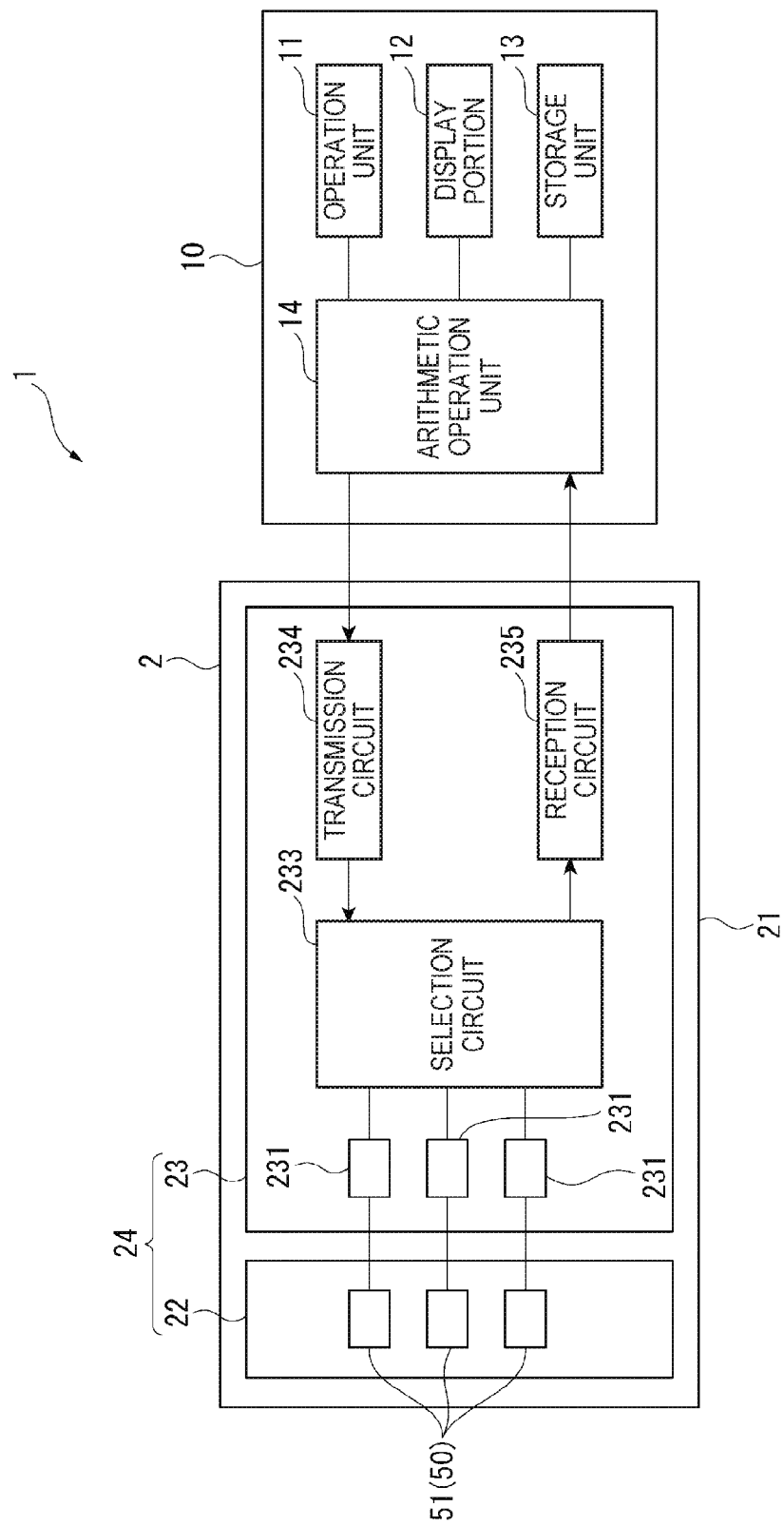
FIG. 2 is a block diagram showing a schematic configuration of the ultrasonic measurement apparatus according to the first embodiment.

FIG. 2 is a block diagram showing a schematic configuration of the ultrasonic measurement apparatus 1.

The control device 10 is configured to include, for example, an operation unit 11, a display portion 12, a storage unit 13, and an arithmetic operation unit 14, as shown in FIG. 2. The control device 10 to be used may be a terminal device such as a tablet terminal, a smart phone, or a personal computer, or may be a dedicated terminal device for operating the ultrasonic probe 2.

The operation unit 11 is a user interface (UI) which is used for a user to operate the ultrasonic measurement apparatus 1, and can be constituted by, for example, a touch panel provided on the display portion 12, operation buttons, a keyboard, a mouse, or the like.

The display portion 12 is constituted by, for example, a liquid crystal display or the like, and displays an image.

The storage unit 13 stores various programs and various pieces of data for controlling the ultrasonic measurement apparatus 1.

The arithmetic operation unit 14 is constituted by, for example, an arithmetic circuit such as a central processing unit (CPU), or a storage circuit such as a memory. The arithmetic operation unit 14 reads and executes various programs stored in the storage unit 13 to thereby perform control of generating and outputting a transmission signal to a transmission circuit 234 of the ultrasonic probe 2 and perform control of setting a frequency or a gain of a received signal on a reception circuit 235.

Configuration of Ultrasonic Probe 2

Figure 3:
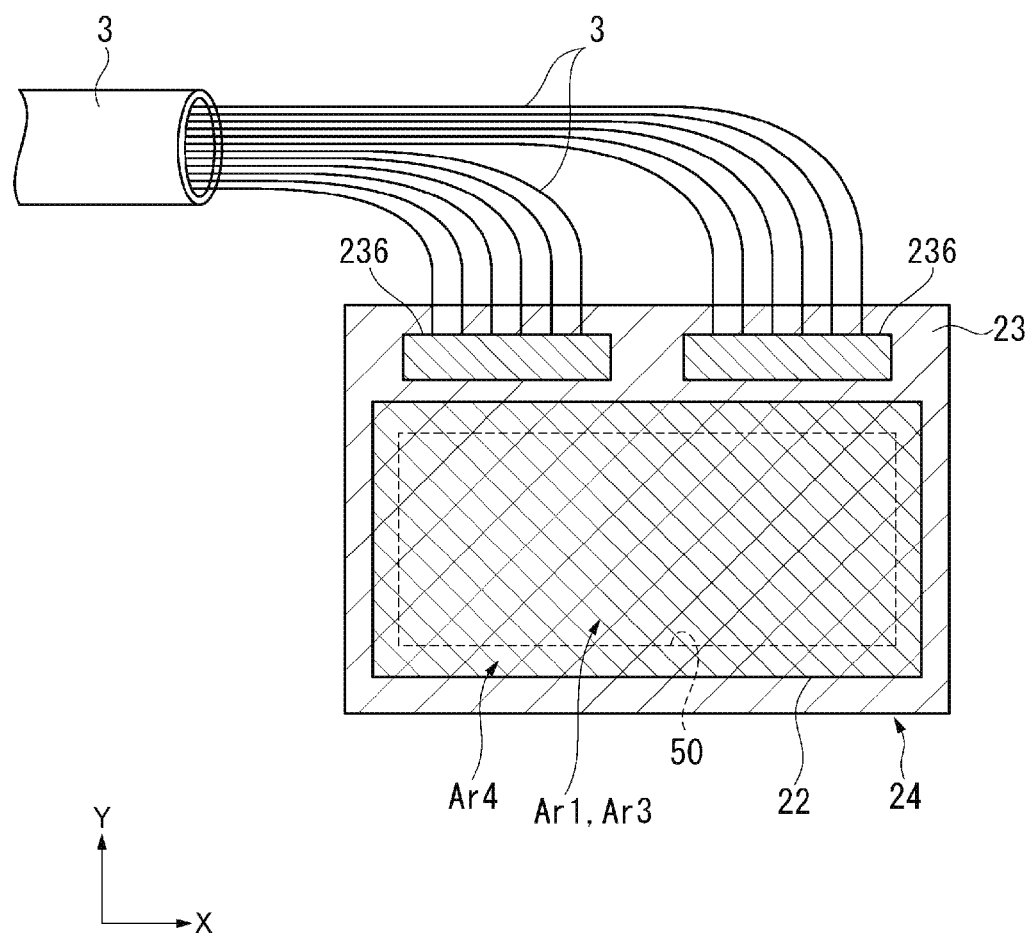
FIG. 3 is a plan view showing a schematic configuration of an ultrasonic sensor in an ultrasonic probe according to the first embodiment.

FIG. 3 is a plan view showing a schematic configuration of the ultrasonic sensor 24 in the ultrasonic probe 2.

The ultrasonic probe 2 includes a housing 21, an ultrasonic device 22 provided inside the housing 21, and a wiring substrate 23 provided with a driver circuit for controlling the ultrasonic device 22, and the like, as shown in FIGS. 1 to 3. Meanwhile, the ultrasonic sensor 24 is constituted by the ultrasonic device 22 and the wiring substrate 23, and the ultrasonic sensor 24 constitutes an ultrasonic module according to the invention.

Configuration of Housing 21

The housing 21 is formed to have a rectangular box shape when seen in a plan view, as shown in FIG. 1, and is configured such that a sensor window 21B is provided on one surface (sensor surface 21A) thereof which is perpendicular to the thickness direction, and a portion of the ultrasonic device 22 is exposed. In addition, a portion (a side surface in the example shown in FIG. 1) of the housing 21 is provided with a passing hole 21C of the cable 3, and the cable 3 is connected to the wiring substrate 23 within the housing 21 from the passing hole 21C. In addition, a gap between the cable 3 and the passing hole 21C is filled with, for example, a resin material, and thus a waterproofing property is secured.

Meanwhile, in this embodiment, a description is given of a configuration example in which the ultrasonic probe 2 and the control device 10 are connected to each other through the cable 3, as shown in FIG. 3, but the invention is not limited thereto. For example, the ultrasonic probe 2 and the control device 10 may be connected to each other through wireless communication, or various components of the control device 10 may be provided within the ultrasonic probe 2.

The ultrasonic device 22 constitutes the ultrasonic sensor 24 together with the wiring substrate 23, as described above. The ultrasonic device 22 includes an ultrasonic transducer array 50 in which a plurality of ultrasonic transducers 51 (see FIG. 4) are arranged in an array, as shown in FIGS. 2 and 3.

Meanwhile, a detailed configuration of the ultrasonic device 22 will be described later.

Configuration of Wiring Substrate 23

The wiring substrate 23 includes a wiring terminal 231, a bonding member 232 (see FIG. 5), a selection circuit 233, a transmission circuit 234, a reception circuit 235, and a connector unit 236, as shown in FIGS. 2 and 3. Among these, the selection circuit 233, the transmission circuit 234, the reception circuit 235, and the connector unit 236 constitute a driver circuit for driving the ultrasonic device 22, or the like, that is, an integrated circuit IC (see FIG. 5). The integrated circuit IC is equivalent to an input and output circuit according to the invention.

A plurality of wiring terminals 231 are disposed on the wiring substrate 23, and are electrically connected to the above-mentioned integrated circuit IC. Each of the plurality of wiring terminals 231 is connected to the ultrasonic transducer 51, more specifically, a first through electrodes 423 or a second through electrodes 424 to be described later through the bonding member 232.

The selection circuit 233 switches between transmission connection for connecting the ultrasonic device 22 and the transmission circuit 234 to each other and reception connection for connecting the ultrasonic device 22 and the reception circuit 235 to each other under the control of the control device 10.

The transmission circuit 234 outputs a transmission signal indicating that ultrasonic waves are transmitted to the ultrasonic device 22 through the selection circuit 233 at the time of being switched to transmission connection under the control of the control device 10.

The reception circuit 235 outputs a received signal which is input from the ultrasonic device 22 through the selection circuit 233 to the control device 10 at the time of being switched to reception connection under the control of the control device 10. The reception circuit 235, which is configured to include, for example, a low noise amplifier circuit, a voltage control attenuator, a programmable gain amplifier, a low-pass filter, an A/D converter, and the like, performs each signal processing, such as conversion of a received signal into a digital signal, removal of a noise component, and amplification to a desired signal level, and then outputs the processed received signal to the control device 10.

The connector unit 236 is connected to the transmission circuit 234 and the reception circuit 235. In addition, the cable 3 is connected to the connector unit 236, and the cable 3 is drawn from the passing hole 21C of the housing 21 and is connected to the control device 10, as described above.

Configuration of Ultrasonic Device 22

Figure 4:
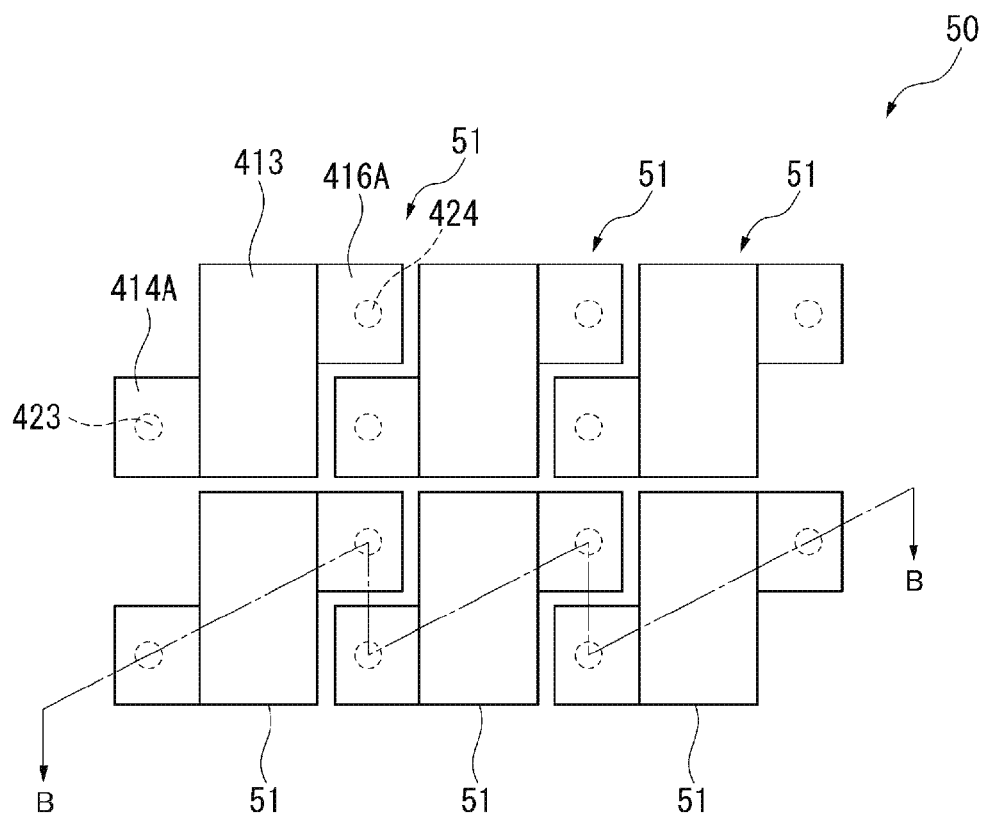
FIG. 4 is an enlarged plan view of a portion of an element substrate of the ultrasonic sensor according to the first embodiment.
Figure 5:
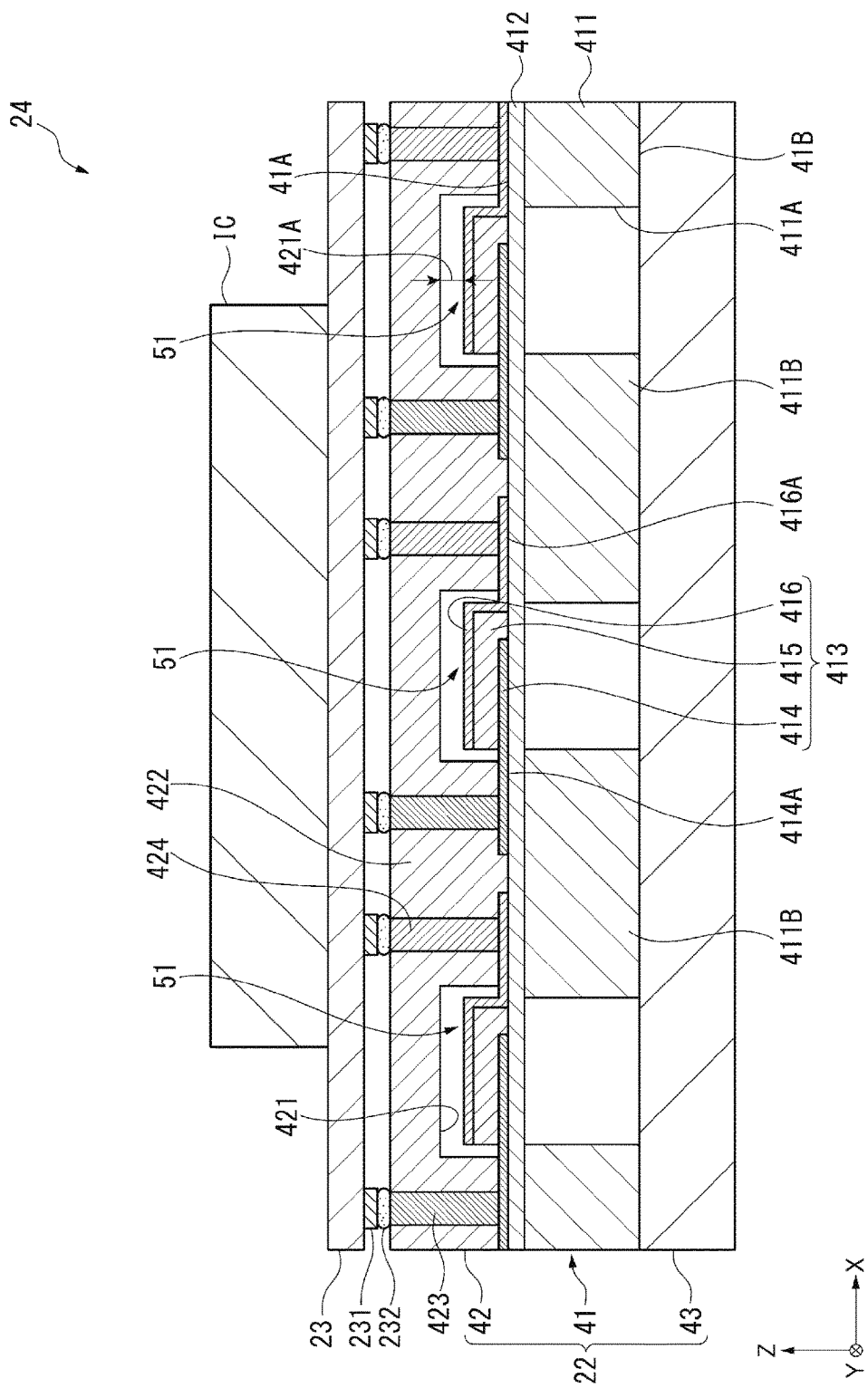
FIG. 5 is a cross-sectional view of a portion of the ultrasonic sensor according to the first embodiment.

FIG. 4 is an enlarged plan view of a portion of an element substrate 41 of the ultrasonic probe 2 according to this embodiment, and FIG. 5 is a cross-sectional view of the element substrate 41 (ultrasonic sensor 24) when a portion of the element substrate 41 in FIG. 4 is taken along line B-B.

The ultrasonic device 22 constituting the ultrasonic sensor 24 is constituted by the element substrate 41, a sealing plate 42, and an acoustic matching layer 43 (see FIG. 5), as shown in FIGS. 3 and 4.

Meanwhile, the sealing plate 42 is equivalent to a reinforcement plate according to the invention.

Configuration of Element Substrate 41

The element substrate 41 includes a substrate main body 411, a vibration film 412 laminated on the substrate main body 411, and a piezoelectric element 413 laminated on the vibration film 412, as shown in FIG. 5. Here, in the element substrate 41, a back surface 41A facing the sealing plate 42 is a second surface according to the invention, and an operating surface 41B serving as a transmission and reception direction of ultrasonic waves on a side opposite to the back surface 41A is a first surface according to the invention. In addition, the ultrasonic transducer 51 according to the invention is constituted by the vibration film 412 and the piezoelectric element 413.

As shown in FIG. 4, a central region of the element substrate 41 is provided with the ultrasonic transducer array 50 in which the plurality of ultrasonic transducers 51 are arranged in an array, in a plan view when the element substrate 41 is seen from a thickness direction. Hereinafter, the region provided with the ultrasonic transducer array 50 will be referred to as an array region Ar1 (see FIG. 3).

The substrate main body 411 is a semiconductor substrate such as Si. Openings 411A corresponding to the respective ultrasonic transducers 51 are provided within an array region Ar1 of the substrate main body 411. In addition, the openings 411A are closed by the vibration film 412 provided on the back surface 41A side of the substrate main body 411.

The vibration film 412 is constituted by, for example, SiO$_2$ or a laminated body of SiO$_2$ and ZrO$_2$, and is provided so as to cover the entire back surface 41A side of the substrate main body 411. A thickness dimension of the vibration film 412 is sufficiently smaller than that of the substrate main body 411. In a case where the substrate main body 411 is formed of Si and the vibration film 412 is formed of SiO$_2$, it is possible to easily form the vibration film 412 with a desired thickness dimension, for example, by oxidizing the back surface 41A side of the substrate main body 411. In this case, it is possible to easily form the opening 411A by etching the substrate main body 411 using the vibration film 412 formed of SiO$_2$ as an etching stopper.

Meanwhile, a recessed opening according to the invention is constituted by the opening 411A and a region that closes the opening 411A in the vibration film 412. In addition, a portion which is not provided with the opening 411A in the element substrate 41 is a supporting portion 411B that surrounds the opening 411A when seen in a plan view.

In addition, the piezoelectric element 413 which is a laminated body of a lower electrode 414, a piezoelectric film 415, and an upper electrode 416, which are independently provided, is provided on the vibration film 412 that closes the openings 411A, as shown in FIG. 5. Meanwhile, the piezoelectric element 413 is equivalent to a piezoelectric body according to the invention. In addition, the ultrasonic transducer 51 is constituted by the vibration film 412 and the piezoelectric element 413, and the ultrasonic transducer is equivalent to an element unit according to the invention.

In the ultrasonic transducer 51, a rectangular wave voltage with a predetermined frequency is applied between the lower electrode 414 and the upper electrode 416, and thus it is possible to vibrate the vibration film 412 within an opening region of the opening 411A and to transmit ultrasonic waves. In addition, when the vibration film 412 is vibrated by ultrasonic waves reflected from an object, a potential difference occurs between upper and lower sides of the piezoelectric film 415. Therefore, it is possible to detect received ultrasonic waves by detecting the potential difference occurring between the lower electrode 414 and the upper electrode 416.

In addition, the lower electrode 414 is independently provided for each piezoelectric element 413, and the upper electrode 416 is independently provided for each piezoelectric element 413, similar to the lower electrode 414.

Meanwhile, the first through electrode 423 to be described later is electrically connected to each of the lower electrodes 414, and the second through electrode 424 to be described later is electrically connected to each of the upper electrodes 416.

In addition, in this embodiment, as shown in FIG. 4, the plurality of ultrasonic transducers 51 mentioned above are disposed within the array region Ar1 of the element substrate 41 along an X-direction (first direction) and a Y-direction (second direction) perpendicular to the X-direction.

Specifically, regarding the piezoelectric element 413 constituting the ultrasonic transducer 51 is drawn from a lower connection electrode 414A (equivalent to a third connection electrode according to the invention) is drawn toward the −X side from an end on the −Y side at an end side on the −X side of the lower electrode 414 that overlaps the piezoelectric film 415, as shown in FIG. 4. In addition, an upper connection electrode 416A (equivalent to a fourth connection electrode according to the invention) is drawn toward the +X side from the +Y side at an end side on the +X side of the upper electrode 416 that overlaps the piezoelectric film 415. That is, in a case where the piezoelectric element 413 is seen along the Y-direction, the upper electrode 416 of the piezoelectric element 413 positioned on the −X side and the lower electrode 414 of the piezoelectric element 413 positioned on the +X side are disposed so as to overlap each other between two piezoelectric elements 413 that are adjacent to each other along the X-direction.

With such a configuration, it is possible to densely dispose the piezoelectric elements 413, as compared to a case where the lower connection electrode 414A is drawn toward the −X side from a central portion of an end side on the −X side of the piezoelectric element 413, and the upper connection electrode 416A is drawn toward the +X side from the central portion of the end side on the +X side (the lower electrode 414 and the upper electrode 416 do not overlap each other when seen along the Y-direction).

Configuration of Sealing Plate 42

The sealing plate 42 is configured such that the planar shape thereof when seen from the thickness direction is the same shape as that of, for example, the element substrate 41, and is constituted by a semiconductor substrate such as a silicon substrate, or an insulating substrate. Meanwhile, the material and thickness of the sealing plate 42 have influence on frequency characteristics of the ultrasonic transducer 51, and thus are preferably set on the basis of the center frequency of ultrasonic waves transmitted and received by the ultrasonic transducer 51.

In the sealing plate 42, a plurality of concave grooves 421 corresponding to the openings 411A of the element substrate 41 are formed in an array counter region Ar3 (See FIG. 3) which faces the array region Ar1 of the element substrate 41. Thereby, in the vibration film 412, a gap 421A having a predetermined dimension is provided with respect to the element substrate 41 in a region (within the opening 411A) which is vibrated by the ultrasonic transducer 51, and thus the vibration of the vibration film 412 is not obstructed. In addition, it is possible to suppress a defect (crosstalk) in which back waves from one ultrasonic transducer 51 are incident on another adjacent ultrasonic transducer 51.

Meanwhile, a region (the supporting portion 411B; see FIG. 5) of the substrate main body 411 other than the opening 411A and a region of the sealing plate 42 other than the concave groove 421 may abut against each other or may be bonded to each other.

In addition, when the vibration film 412 vibrates, ultrasonic waves as back waves are radiated not only to the opening 411A side (operating surface 41B side) but also to the sealing plate 42 side (back surface 41A side). The back waves are reflected by the sealing plate 42, and are radiated to the vibration film 412 side again through the gap 421A. At this time, when phases of the reflected back waves and the ultrasonic waves radiated to the operating surface 41B side from the vibration film 412 deviate, the ultrasonic waves are attenuated. Therefore, in this embodiment, the depth of each of the concave grooves 421 is set so that an acoustic distance in the gap 421A is set to be odd number times a quarter of a wavelength $\lambda$ ($\lambda/4$) of an ultrasonic wave. In other words, the thickness dimension of each portion of the element substrate 41 and the sealing plate 42 is set in consideration of the wavelength λ of the ultrasonic wave emitted from the ultrasonic transducer 51.

In addition, in the sealing plate 42, a reinforcement portion 422 facing the supporting portion 411B is bonded to the element substrate 41 to thereby reinforce the element substrate 41. In the reinforcement portion 422, a through hole is provided at each of positions that face the lower connection electrodes 414A and the upper connection electrodes 416A, and through electrodes (the first through electrode 423 and the second through electrode 424) are provided in the through hole.

The first through electrode 423 passes through the sealing plate 42 in the thickness direction to be connected to the lower connection electrode 414A. The first through electrode 423 is provided corresponding to each of the plurality of lower connection electrodes 414A. Therefore, an independent signal can be input and output with respect to each of the lower electrodes 414 through the lower connection electrode 414A from the first through electrode 423.

Similarly, the second through electrode 424 passes through the sealing plate 42 in the thickness direction to be connected to the upper connection electrode 416A. The second through electrode 424 is provided corresponding to each of the plurality of upper connection electrodes 416A, and an independent signal can be input and output with respect to each of the upper electrodes 416 through the upper connection electrode 416A from the second through electrode 424.

Connection of the first through electrode 423 and the lower connection electrode 414A, and connection of the second through electrode 424 and the upper connection electrode 416A may be performed through bonding using a conductive bonding member (not shown) such as solder, or may be performed through bonding using an anisotropic conductive film (ACF) or anisotropic conductive paste (ACP). In a case where an ACF or ACP is used, the ACF is formed on, for example, a surface facing the element substrate 41 of the reinforcement portion 422 of the sealing plate 42, or the ACP is applied thereto. Then, the sealing plate 42 is superimposed on the element substrate 41 to apply a load in the thickness direction. Thereby, conductivity is held in a load application direction (thickness direction) of the ACF (or ACP), and an insulating property is held in a direction perpendicular to the application of a load. That is, the first through electrode 423 and the lower connection electrode 414A are electrically connected to each other, the second through electrode 424 and the upper connection electrode 416A are electrically connected to each other, and the element substrate 41 and the sealing plate 42 are bonded to each other by an ACF (or ACP).

In addition, the other end sides (sides opposite to the element substrate 41) of the first through electrodes 423 and the second through electrodes 424 are connected to the wiring terminals 231 of the wiring substrate 23 through the conductive bonding member 232 such as solder. The wiring terminals 231 are independently formed on the wiring substrate 23, and are independently controlled by the above-mentioned integrated circuit IC. That is, in this embodiment, the ultrasonic transducers 51 can be independently controlled through the first through electrodes 423 and the second through electrodes 424. In other words, ultrasonic waves can be transmitted at each timing from a CAV surface (surface on a side to which the opening 411A in the element substrate 41 opens) of each of the ultrasonic transducers 51.

In this case, for example, a transmission timing of ultrasonic waves to be transmitted from the ultrasonic transducers 51 lined up in the X-direction is delayed with a direction perpendicular to the X-direction and the Y-direction as a Z-direction (a normal direction of a substrate surface of the element substrate 41 (substrate thickness direction)), and thus it is possible to control a transmission direction of the ultrasonic waves in an XZ plane. In addition, for example, a transmission timing of ultrasonic waves to be transmitted from the ultrasonic transducers 51 lined up in the Y-direction is delayed, and thus it is possible to control a transmission direction of the ultrasonic waves in a YZ plane. That is, the ultrasonic transducer array 50 can be made to function as a two-dimensional array, and thus it is possible to transmit ultrasonic waves in any direction. For this reason, in this embodiment, an acoustic lens that refracts ultrasonic waves to control a transmission direction to a predetermined direction is not provided.

Configuration of Acoustic Matching Layer 43

The acoustic matching layer 43 is provided on the operating surface 41B side of the element substrate 41, as shown in FIG. 5. Specifically, the acoustic matching layer 43 is filled into the opening 411A of the element substrate 41, and is formed to have a predetermined thickness dimension from the operating surface 41B side of the substrate main body 411.

The acoustic matching layer 43 efficiently propagates ultrasonic waves transmitted from the ultrasonic transducer 51 to a living body which is an object to be measured, and efficiently propagates the ultrasonic wave reflected within the living body to the ultrasonic transducer 51. For this reason, the acoustic matching layer 43 is set to intermediate acoustic impedance between acoustic impedance of the ultrasonic transducer 51 of the element substrate 41 and acoustic impedance of the living body.

Operational Effects of First Embodiment

In this embodiment, the opening 411A is provided in the substrate main body 411, and the vibration film 412 closing the opening 411A is provided on the back surface 41A side (second surface side) of the substrate main body 411. In other words, a recessed opening constituted by the opening 411A and the vibration film 412 is provided on the operating surface 41B (first surface) of the element substrate 41. In addition, the piezoelectric element 413 is provided on the back surface 41A side of the vibration film 412 which is the bottom face of the recessed opening. The lower connection electrode 414A connected to the lower electrode 414 of the piezoelectric element 413 and the upper connection electrode 416A connected to the upper electrode 416 are drawn to the supporting portion 411B (a region other than a region in which the opening 411A is provided in the element substrate 41) of the element substrate 41. The lower connection electrode 414A and the upper connection electrode 416A are connected to the first through electrode 423 and the second through electrode 424 that pass through the sealing plate 42 bonded to the back surface 41A side of the element substrate 41 in the thickness direction.

In such a configuration, a signal is input and output with respect to each of the ultrasonic transducers 51 from the first through electrode 423 and the second through electrode 424, and thus it is possible to individually control the ultrasonic transducers 51. In addition, since the first through electrode 423 and the second through electrode 424 are configured to be provided in the sealing plate 42 rather than being provided in the element substrate 41, a through hole is not required to be provided in the element substrate 41, and thus it is possible to suppress the damage of the element substrate 41 due to an impact or the like.

In this embodiment, the lower electrode 414 and the upper electrode 416 provided in the element substrate 41 are electrically connected to the first through electrode 423 and the second through electrode 424 through the lower connection electrode 414A and the upper connection electrode 416A, and the first through electrode 423 and the second through electrode 424 pass through to a side of the sealing plate 42 which is opposite to the element substrate 41.

In such a configuration, since the first through electrode 423 and the second through electrode 424 are configured to be provided within the ultrasonic transducer array 50, the pulling-around of a wiring, and the like are not required, and thus it is possible to reduce the size of the ultrasonic device 22 and to promote reductions in the sizes of the ultrasonic sensor 24 and the ultrasonic probe 2.

In this embodiment, when a signal is independently input and output with respect to each of the first through electrode 423 and the second through electrode 424 from the integrated circuit IC, it is possible to individually control the piezoelectric elements 413 (the ultrasonic transducers 51). In addition, the ultrasonic transducers 51 are disposed in a two-dimensional array structure along the X-direction and the Y-direction. For this reason, it is possible to transmit ultrasonic waves in any direction and to eliminate the necessity of a configuration such as an acoustic lens by controlling a driving timing of each of the ultrasonic transducers 51.

In this embodiment, the lower connection electrode 414A is drawn from the −Y side to the −X side at an end side on the −X side of the piezoelectric element 413. In addition, the upper connection electrode 416A is drawn from the +Y side to the +X side at an end side on the +X side of the piezoelectric element 413. Accordingly, in piezoelectric elements 413 (ultrasonic transducers 51) that are adjacent to each other in the X-direction, an upper connection electrode 416A of the piezoelectric element 413 disposed on the −X side and a lower connection electrode 414A of the piezoelectric element 413 disposed on the +X side can be disposed side by side along the Y-direction. With such a configuration, in the ultrasonic transducer array 50, it is possible to densely dispose the ultrasonic transducers 51, to make the ultrasonic transducer array 50 and the ultrasonic device 22 smaller, and to promote further reductions in the sizes of the ultrasonic sensor 24 and the ultrasonic probe 2.

The ultrasonic probe 2 in this embodiment is a so-called CAV surface emitting ultrasonic probe that transmits ultrasonic waves from a CAV surface, and the piezoelectric element 413, the lower connection electrode 414A, and the upper connection electrode 416A are disposed on a side opposite to an ultrasonic wave emission side in the vibration film 412. In a case where the measurement of ultrasonic waves is performed on a living body using the ultrasonic probe 2, gel is applied between the acoustic matching layer 43 and the living body, but drops of water may be normally infiltrated between the acoustic matching layer 43 and the vibration film 412. However, as described above, in this embodiment, the piezoelectric element 413, the lower connection electrode 414A, and the upper connection electrode 416A are disposed on the back surface 41A side of the vibration film 412, and thus do not come into contact with drops of water, and thus it is possible to suppress defects such as a short-circuit and rust.

Second Embodiment

Next, a second embodiment of the invention will be described.

An ultrasonic measurement apparatus according to this embodiment has substantially the same configuration as that of the ultrasonic measurement apparatus 1 described above, and is different from the ultrasonic measurement apparatus 1 in that a portion of a configuration of a piezoelectric element 413 constituting an ultrasonic transducer is different.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 6:
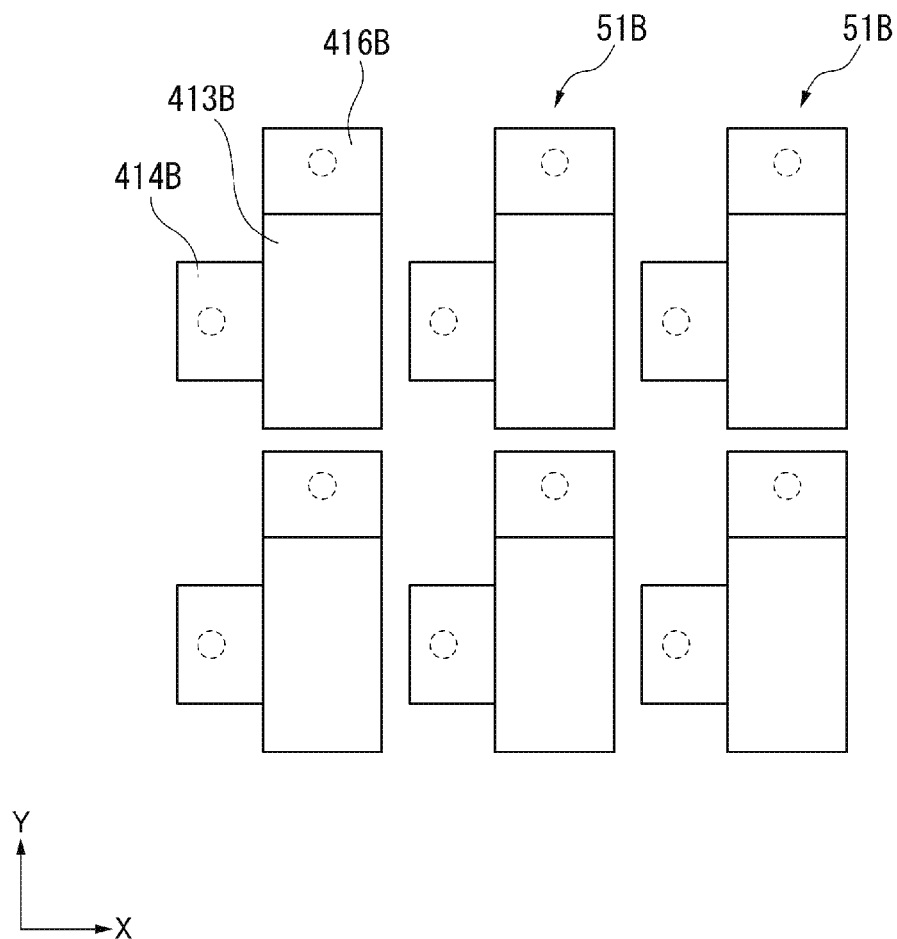
FIG. 6 is an enlarged plan view of a portion of an element substrate of an ultrasonic sensor of an ultrasonic measurement apparatus according to a second embodiment.

FIG. 6 is an enlarged plan view of a portion of an element substrate of an ultrasonic sensor of the ultrasonic measurement apparatus according to this embodiment.

In this embodiment, as shown in FIG. 6, a plurality of ultrasonic transducers 51B mentioned above are disposed along an X-direction (first direction) and a Y-direction (second direction) which is perpendicular to the X-direction within an array region Ar1 of an element substrate 41.

In this embodiment, a lower connection electrode 414B is drawn to the −X side of a lower electrode 414 that overlaps a piezoelectric film 415 in FIG. 6. On the other hand, an upper connection electrode 416B is drawn to the +Y side of an upper electrode 416 that overlaps the piezoelectric film 415. In this embodiment, the lower connection electrode 414B is equivalent to a first connection electrode according to the invention, and the upper connection electrode 416B is equivalent to a second connection electrode according to the invention.

Meanwhile, in the above-mentioned example, a description is given of an example in which the lower connection electrode 414B is drawn to the −X side of the lower electrode 414, and the upper connection electrode 416B is drawn to the +Y side of the upper electrode 416, but the invention is not limited thereto.

For example, the lower connection electrode 414B may be drawn to the −X side of the lower electrode 414, the upper connection electrode 416B may be drawn to the −Y side of the upper electrode 416, the lower connection electrode 414B may be drawn to the +X side of the lower electrode 414, the upper connection electrode 416B may be drawn to the −Y side of the upper electrode 416, the lower connection electrode 414B may be drawn to the +X side of the lower electrode 414, and the upper connection electrode 416B may be drawn to the +Y side of the upper electrode 416.

In addition, drawing directions of the lower connection electrode 414B and the upper connection electrode 416B may be switched to each other. For example, the lower connection electrode 414B may be drawn to the −Y side of the lower electrode 414, the upper connection electrode 416B may be drawn to the +X side of the upper electrode 416, the lower connection electrode 414B may be drawn to the −Y side of the lower electrode 414, the upper connection electrode 416B may be drawn to the −X side of the upper electrode 416, the lower connection electrode 414B may be drawn to the +Y side of the lower electrode 414, the upper connection electrode 416B may be drawn to the −X side of the upper electrode 416, the lower connection electrode 414B may be drawn to the +Y side of the lower electrode 414, and the upper connection electrode 416B may be drawn to the +X side of the upper electrode 416.

Operational Effects of Second Embodiment

In this embodiment, a piezoelectric element 413B constituting the ultrasonic transducer 51B includes the lower connection electrode 414B which is drawn to the −X side and the upper connection electrode 416B which is drawn to the +Y side. In this case, when piezoelectric elements 413C are arranged along the X-direction and the Y-direction, one lower connection electrode 414B is disposed between piezoelectric elements 413B that are aligned in the X-direction, and one upper connection electrode 416B is disposed between piezoelectric elements 413B that are aligned in the Y-direction. Accordingly, it is possible to densely dispose the piezoelectric elements 413B (ultrasonic transducers 51B), for example, as compared to a case where a plurality of (for example, two) connection electrodes are disposed between piezoelectric elements. Thereby, similarly to the above-described first embodiment, it is possible to make an ultrasonic transducer array 50 and an ultrasonic device 22 smaller and to promote further reductions in the sizes of an ultrasonic sensor 24 and an ultrasonic probe 2.

Third Embodiment

Next, a third embodiment of the invention will be described.

An ultrasonic measurement apparatus according to this embodiment has substantially the same configuration as that of the ultrasonic measurement apparatus 1 described above, and is different from the ultrasonic measurement apparatus 1 in that a portion of a configuration of a piezoelectric element 413 constituting an ultrasonic transducer is different.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 7:
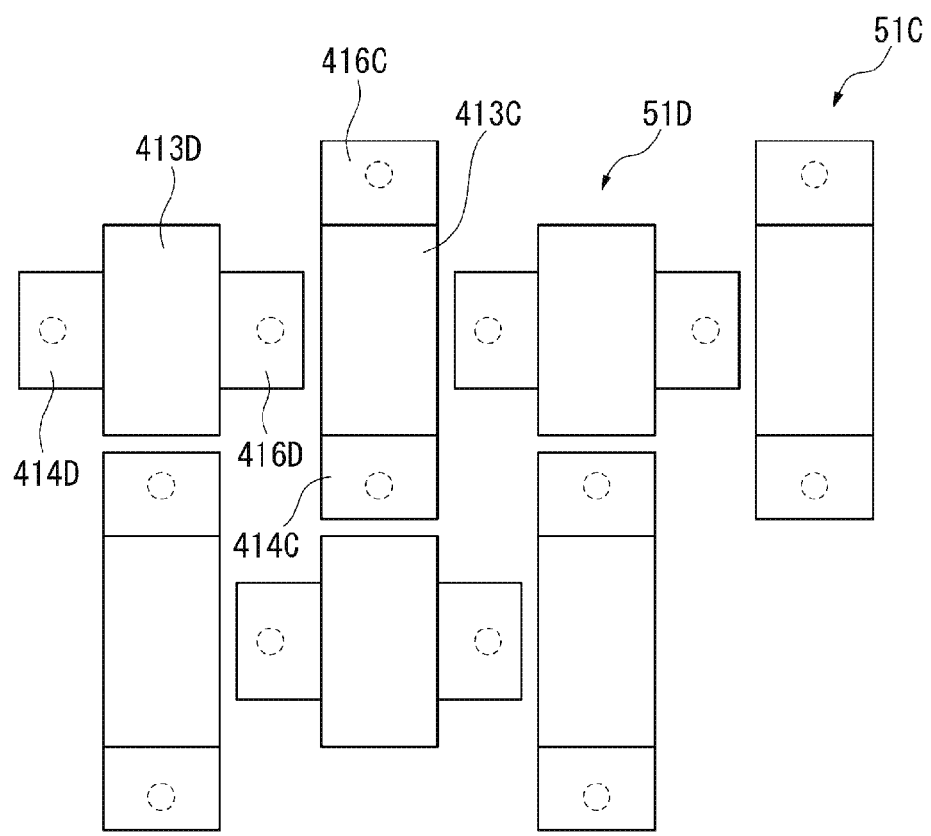
FIG. 7 is an enlarged plan view of a portion of an element substrate of an ultrasonic sensor of an ultrasonic measurement apparatus according to a third embodiment.

FIG. 7 is an enlarged plan view of a portion of an element substrate of an ultrasonic sensor of the ultrasonic measurement apparatus according to the embodiment.

In this embodiment, as shown in FIG. 7, a plurality of ultrasonic transducers 51C and 51D are disposed along an X-direction (first direction) and a Y-direction (second direction) which is perpendicular to the X-direction within an array region Ar1 of an element substrate 41.

Specifically, as shown in FIG. 7, in a piezoelectric element 413C constituting the ultrasonic transducer 51C, a lower connection electrode 414C is drawn to a −Y side of a lower electrode 414 that overlaps a piezoelectric film 415, and an upper connection electrode 416C is drawn to the +Y side of an upper electrode 416 that overlaps the piezoelectric film 415.

On the other hand, in a piezoelectric element 413D constituting the ultrasonic transducer 51D, a lower connection electrode 414D is drawn to the −X side of the lower electrode 414 that overlaps the piezoelectric film 415, and an upper connection electrode 416D is drawn to the +X side from the upper electrode 416 that overlaps the piezoelectric film 415. In this embodiment, the piezoelectric element 413D is equivalent to a first piezoelectric element according to the invention, and the piezoelectric element 413C is equivalent to a second piezoelectric element according to the invention.

Meanwhile, in the above-mentioned example, the lower connection electrode 414C is drawn to the −Y side and the upper connection electrode 416C is drawn to the +Y side in the piezoelectric element 413C, but the lower connection electrode 414C may be drawn to the +Y side, and the upper connection electrode 416C may be drawn to the −Y side. Similarly, the lower connection electrode 414D is drawn to the −X side and the upper connection electrode 416D is drawn to the +X side in the piezoelectric element 413D, but the lower connection electrode 414D may be drawn to the +X side, and the upper connection electrode 416D may be drawn to the −X side.

Operational Effects of Third Embodiment

In this embodiment, the lower connection electrode 414C and the upper connection electrode 416C are drawn along the Y-direction in the piezoelectric element 413C constituting the ultrasonic transducer 51C out of the ultrasonic transducers 51C and 51D, and the lower connection electrode 414D and the upper connection electrode 416D are drawn along the X-direction in the piezoelectric element 413D constituting the ultrasonic transducer 51D. The ultrasonic transducers 51C and 51D are alternately disposed in the X-direction and the Y-direction. In such a configuration, one lower connection electrode 414C or one upper connection electrode 416C is disposed between piezoelectric elements 413C that are aligned in the X-direction, and one lower connection electrode 414D or one upper connection electrode 416D is disposed between piezoelectric elements 413D that are aligned in the Y-direction. Accordingly, it is possible to densely dispose the piezoelectric elements 413C and 413D (ultrasonic transducers 51C and 51D), for example, as compared to a case where a plurality of (for example, two) connection electrodes are disposed between piezoelectric elements. Thereby, similarly to the above-described first embodiment, it is possible to make an ultrasonic transducer array 50 and an ultrasonic device 22 smaller and to promote further reductions in the sizes of an ultrasonic sensor 24 and an ultrasonic probe 2.

Fourth Embodiment

Next, a fourth embodiment of the invention will be described.

An ultrasonic measurement apparatus according to this embodiment has substantially the same configuration as that of the ultrasonic measurement apparatus 1 described above, and is different from the ultrasonic measurement apparatus 1 in that a portion of a configuration of a piezoelectric element 413 constituting an ultrasonic transducer is different.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 8:
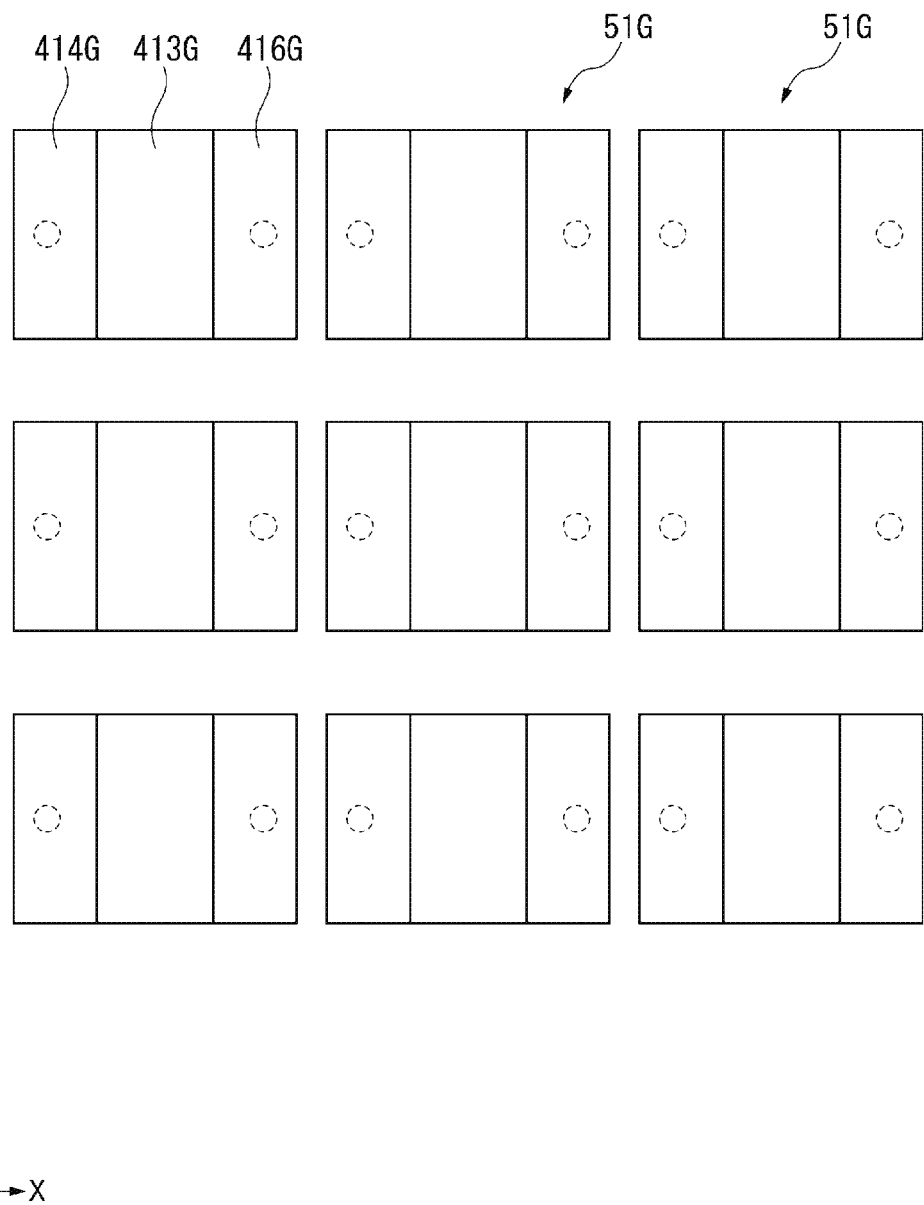
FIG. 8 is an enlarged plan view of a portion of an element substrate of an ultrasonic sensor of an ultrasonic measurement apparatus according to a fourth embodiment.

FIG. 8 is an enlarged plan view of a portion of an element substrate of an ultrasonic sensor of the ultrasonic measurement apparatus according to this embodiment.

In this embodiment, as shown in FIG. 8, a plurality of ultrasonic transducers 51G mentioned above are disposed along an X-direction (first direction) and a Y-direction (second direction) which is perpendicular to the X-direction within an array region Ar1 of an element substrate 41.

Specifically, in a piezoelectric element 413G constituting the ultrasonic transducer 51G, a lower connection electrode 414G is drawn to the −X side, and an upper connection electrode 416G is drawn to the +X side, as shown in FIG. 8.

Operational Effects of Fourth Embodiment

In this embodiment, the piezoelectric element 413G constituting the ultrasonic transducer 51G is configured such that the lower electrode 414 is positioned on the −X-direction side of the piezoelectric film 415 with respect to the piezoelectric film 415, and the upper electrode 416 is positioned on the +X-direction side with respect to the piezoelectric film 415. Accordingly, it is possible to simplify the configuration of the piezoelectric element, for example, as compared to the piezoelectric elements 413, and 413B to 413D in the first to third embodiments.

In addition, it is possible to increase a distance between the piezoelectric elements 413G adjacent to each other. For example, in a case where the frequency of ultrasonic waves to be transmitted and received is a low frequency, it is necessary to increase an opening diameter of the opening 411A. In this case, when a distance between the openings 411A adjacent to each other is short, the strength of the element substrate 41 is reduced. On the other hand, in this embodiment, a distance between the piezoelectric elements 413G is large, the strength of the supporting portion 411B is increased, and thus it is possible to suppress the damage of the element substrate 41.

Modification Example

Meanwhile, the invention is not limited to the above-described embodiments, and configurations obtained by modification, correction, and an appropriate combination of the embodiments within a range in which the object of the invention can be accomplished are included in the invention.

In addition, a description has been given of an example in which the piezoelectric element 413 is constituted by a laminated body in which the lower electrode 414, the piezoelectric film 415, and the upper electrode 416 are laminated in the thickness direction, but the invention is not limited thereto. For example, a configuration may also be adopted in which a pair of electrodes are disposed on one surface side perpendicular to the thickness direction of the piezoelectric element 413 so as to face each other. In addition, electrodes may be disposed so that the piezoelectric film is interposed between side surfaces along the thickness direction of the piezoelectric film.

In the above-described embodiments, a configuration in which the integrated circuit IC is provided on the wiring substrate 23 has been described, but the invention is not limited thereto. For example, a configuration may also be adopted in which the integrated circuit IC is provided within the control device 10, and the wiring substrate 23 is provided with a connector unit in which wirings from the respective wiring terminals 231 are integrated. In this case, a cable line may be connected to the connector unit, and the integrated circuit IC of the control device 10 and the ultrasonic probe 2 may be connected to each other through the cable line.

The ultrasonic measurement apparatus 1 is configured to measure an internal tomographic structure of a living body, but can also be used as a measurement apparatus for inspecting a concrete internal structure such as a concrete building.

In addition, the ultrasonic measurement apparatus 1 including the ultrasonic device 22 has been described, but the invention can also be applied to other electronic apparatuses. For example, the invention can be used for an ultrasonic cleaning machine that transmits ultrasonic waves to an object to be cleaned to clean the object to be cleaned using ultrasonic waves.

Figure 9:
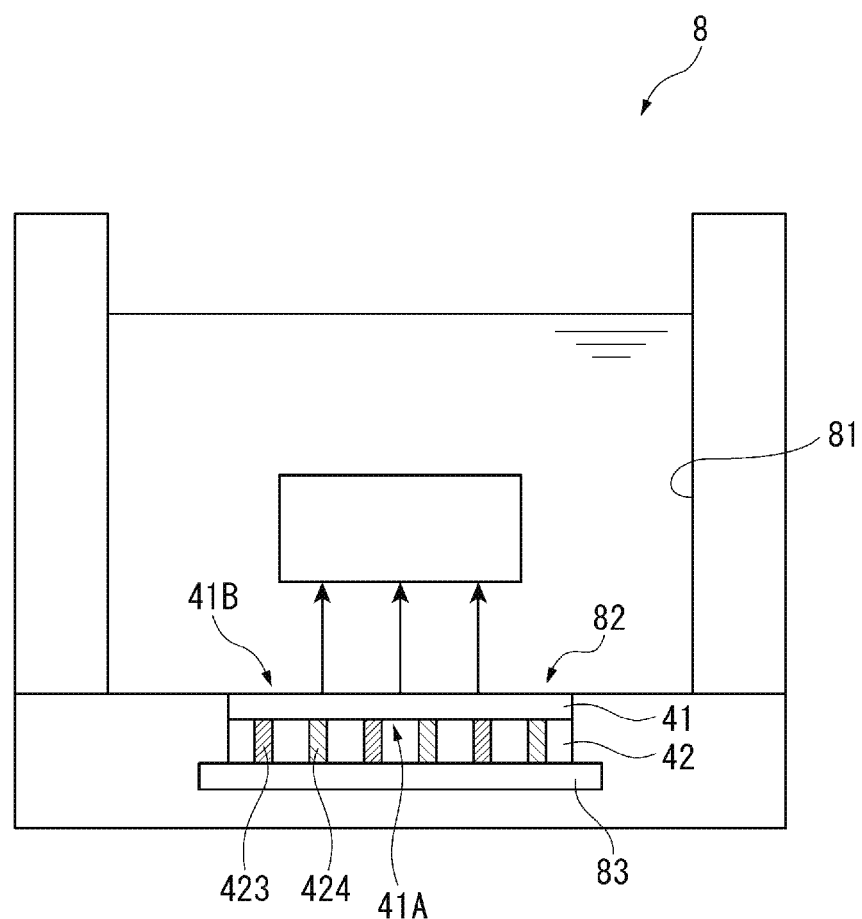
FIG. 9 is a diagram showing an example of an electronic apparatus according to another embodiment.

FIG. 9 is a diagram showing a schematic configuration of an ultrasonic cleaning machine.

An ultrasonic cleaning machine 8 shown in FIG. 9 includes a cleaning tank 81, and an ultrasonic module 82 which is installed on, for example, the bottom face of the cleaning tank 81.

The ultrasonic module 82 includes an ultrasonic device 22 which is the same as that in the above-described embodiments, and a wiring substrate 83 that controls the ultrasonic device 22. That is, the ultrasonic device 22 includes an element substrate 41 in which an operating surface 41B faces the inner surface of the cleaning tank 81, a sealing plate 42 which is provided on a back surface 41A side of the element substrate 41, and an ultrasonic transducer array 50 (not shown in FIG. 9) which is constituted by a plurality of ultrasonic transducers 51 (not shown in FIG. 9) and is provided on the back surface 41A side of the element substrate 41. An upper electrode 416 of a piezoelectric element 413 constituting the ultrasonic transducer 51 is connected to a first through electrode 423 provided in the sealing plate 42, and a lower electrode 414 is connected to a second through electrode 424. The first through electrode 423 and the second through electrode 424 are electrically connected to a wiring terminal (not shown) which is provided in a wiring substrate 83.

In such a configuration, the ultrasonic device 22 can be easily mounted on the wiring substrate 83 by face-down mounting. In addition, since the operating surface 41B side of the element substrate 41 faces the cleaning tank 81 side, it is possible to increase waterproofing properties of the ultrasonic transducer 51 provided on the back surface 41A side and electrode wires.

In the above-described embodiments, a configuration in which the element substrate 41 is provided with the opening 411A has been described. However, for example, a configuration may also be adopted in which the element substrate 41 is not provided with the opening 411A, ultrasonic waves are transmitted by the ultrasonic transducer 51 vibrating the element substrate 41 itself, and the reception of ultrasonic waves is detected by the vibration of the element substrate 41.

In the above-described embodiments, a description has been given of a configuration in which the vibration film 412 is provided on the back surface 41A side of the substrate main body 411 provided with the opening 411A, but the invention is not limited thereto. For example, a configuration may also be adopted in which a plurality of concave grooves corresponding to the respective ultrasonic transducers 51 are provided on the operating surface 41B side of the substrate main body 411, and the bottom face of the concave groove is configured as a vibration film.

In addition, a configuration in which the vibration film 412 is provided on the back surface 41A side of the opening 411A has been described. However, for example, a configuration may also be adopted in which the vibration film 412 is provided on the operating surface 41B side of the opening 411A, and the piezoelectric element 413 constituting the ultrasonic transducer 51 is provided on the back surface 41A side of the vibration film 412.

In addition, a specific structure at the time of implementing the invention may be configured by appropriately combining the above-described embodiments and the modification example within a range in which the object of the invention can be accomplished, or may be appropriately changed to another structure, or the like.

The entire disclosure of Japanese Patent Application No. 2015-234291, filed on Nov. 30, 2015 is expressly incorporated by reference herein.

What is claimed is:
1. A piezoelectric device comprising:
   an element substrate that includes a first surface and a second surface on a side opposite to the first surface, and includes a recessed opening provided on the first surface and a supporting portion surrounding the recessed opening;

a piezoelectric body that is provided on the second surface of the recessed opening;
a plurality of connection electrodes that are connected to the piezoelectric body and are drawn to the second surface of the supporting portion from the piezoelectric body;
a reinforcement plate that is bonded to the second surface side of the element substrate; and
a plurality of through electrodes that are provided at a position of the reinforcement plate which faces the supporting portion, pass through the reinforcement plate in a thickness direction, and are respectively connected to the plurality of connection electrodes.

2. A piezoelectric module comprising:
an element substrate that includes a first surface and a second surface on a side opposite to the first surface, and includes a recessed opening provided on the first surface and a supporting portion surrounding the recessed opening;
a piezoelectric body that is provided on the second surface of the recessed opening;
a plurality of connection electrodes that are connected to the piezoelectric body and are drawn to the second surface of the supporting portion from the piezoelectric body;
a reinforcement plate that is bonded to the second surface side of the element substrate;
a plurality of through electrodes that are provided at a position of the reinforcement plate which faces the supporting portion, pass through the reinforcement plate in a thickness direction, and are respectively connected to the plurality of connection electrodes;
a piezoelectric element substrate that is configured such that element units each of which is constituted by the recessed opening and the piezoelectric body are arranged in an array therein; and
an input and output circuit that independently inputs and outputs a signal from and to each of the through electrodes.

3. The piezoelectric module according to claim 2,
wherein the element units are arranged in an array along a first direction and a second direction intersecting the first direction in a plan view when seen from normal directions of the first surface and the second surface, and
wherein each of the connection electrodes includes a first connection electrode which is drawn from the piezoelectric body along the first direction, and a second connection electrode which is drawn from the piezoelectric body along the second direction.

4. The piezoelectric module according to claim 2,
wherein the element units are arranged in an array along a first direction and a second direction intersecting the first direction in a plan view when seen from normal directions of the first surface and the second surface,
wherein each of the connection electrodes includes a third connection electrode which is drawn to one end side of the piezoelectric body in the first direction, and a fourth connection electrode which is drawn to the other end side of the piezoelectric body in the first direction, and
wherein the third connection electrode is positioned on one end side in the second direction, and the fourth connection electrode is positioned on the other end side in the second direction.

5. The piezoelectric module according to claim 2,
wherein the element units are arranged in an array along a first direction and a second direction intersecting the first direction in a plan view when seen from normal directions of the first surface and the second surface,
wherein the connection electrode connected to a first element unit, among the plurality of elements units, is drawn from the piezoelectric body along the first direction, and
wherein the connection electrode connected to a second element unit, which is adjacent to the first element unit, is drawn from the piezoelectric body along the second direction.

6. An electronic apparatus comprising:
an element substrate that includes a first surface and a second surface on a side opposite to the first surface, and includes a recessed opening provided on the first surface and a supporting portion surrounding the recessed opening;
a piezoelectric body that is provided on the second surface of the recessed opening;
a plurality of connection electrodes that are connected to the piezoelectric body and are drawn to the second surface of the supporting portion from the piezoelectric body;
a reinforcement plate that is bonded to the second surface side of the element substrate;
a plurality of through electrodes that are provided at a position of the reinforcement plate which faces the supporting portion, pass through the reinforcement plate in a thickness direction, and are respectively connected to the plurality of connection electrodes;
a piezoelectric element substrate that is configured such that element units each of which is constituted by the recessed opening and the piezoelectric body are arranged in an array therein;
an input and output circuit that independently inputs and outputs a signal from and to each of the through electrodes; and
a control unit that controls the piezoelectric body.

7. The electronic apparatus according to claim 6,
wherein the control unit performs an ultrasonic wave transmission process of driving the piezoelectric body to transmit ultrasonic waves and an ultrasonic wave reception process of receiving ultrasonic waves by the element units, and measures an object to be measured, on the basis of transmission and reception timings of the ultrasonic waves.

* * * * *